(12) United States Patent
Blank et al.

(10) Patent No.: US 9,260,402 B2
(45) Date of Patent: Feb. 16, 2016

(54) PROCESS FOR THE PREPARATION OF 5-HYDROXYMETHYLFURFURAL (HMF)

(71) Applicant: BASF SE, Ludwigshafen (DE)

(72) Inventors: Benoit Blank, Edingen-Neckarhausen (DE); Alois Kindler, Gruenstadt (DE); Peter Bassler, Viernheim (DE); Markus Piepenbrink, Heidelberg (DE); Ortmund Lang, Quirnbach (DE); Carmen Feldner, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/302,046

(22) Filed: Jun. 11, 2014

(65) Prior Publication Data

US 2014/0371473 A1  Dec. 18, 2014

(30) Foreign Application Priority Data

Jun. 12, 2013 (EP) ..................................... 13171627

(51) Int. Cl.
*C07D 307/46* (2006.01)
*C07D 307/48* (2006.01)
*B01D 3/00* (2006.01)

(52) U.S. Cl.
CPC .............. *C07D 307/46* (2013.01); *B01D 3/009* (2013.01); *C07D 307/48* (2013.01)

(58) Field of Classification Search
CPC .................................................... C07D 307/46
USPC ....................................................... 549/488
See application file for complete search history.

(56) References Cited

FOREIGN PATENT DOCUMENTS

| CN | 101812039 A | 8/2010 |
|---|---|---|
| CN | 102399203 A | 4/2012 |
| WO | WO-92/10486 A1 | 6/1992 |
| WO | WO-2005/018799 A1 | 3/2005 |
| WO | WO-2013/078391 A1 | 5/2013 |

OTHER PUBLICATIONS

International Search Report in international application No. PCT/IB2014/062121 dated Jun. 11, 2014.
Wei, Z., et al, "Entrainer-Intensified Vacuum Reactive Distillation Process for the separation of 5-hydroxylmethylfurfural from the Dehydration of Carbohydrates Catalyzed by a Metal Salt-Ionic liquid." *Green Chemistry*, 2012, vol. 14, No. 7, pp. 1220-1226.
European Search Report in European Patent Application No. EP 13 17 1627, dated Sep. 9, 2013.

*Primary Examiner* — Taofiq A Solola
(74) *Attorney, Agent, or Firm* — Marshall, Gerstein & Borun LLP

(57) ABSTRACT

A process is described for the preparation of 5-hydroxymethylfurfural (HMF), which comprises the following steps:
provision or preparation of a starting mixture, comprising
one, two or more starting compounds selected from the group consisting of hexoses, oligosaccharides comprising hexose units, and polysaccharides comprising hexose units,
one, two or more organic salts with a melting point <180° C. and a boiling point >200° C. at 1013.25 hPa,
optionally additionally one or more catalysts for the conversion of the one starting compound or at least one of the two or more starting compounds to 5-hydroxymethylfurfural (HMF),
optionally water,
optionally further substances,
adjustment of reaction conditions such that an amount of the starting compound or starting compounds converts to HMF.

19 Claims, 2 Drawing Sheets

PROCESS FOR THE PREPARATION OF 5-HYDROXYMETHYLFURFURAL (HMF)

CROSS-REFERENCE TO RELATED APPLICATIONS

Figure 1:
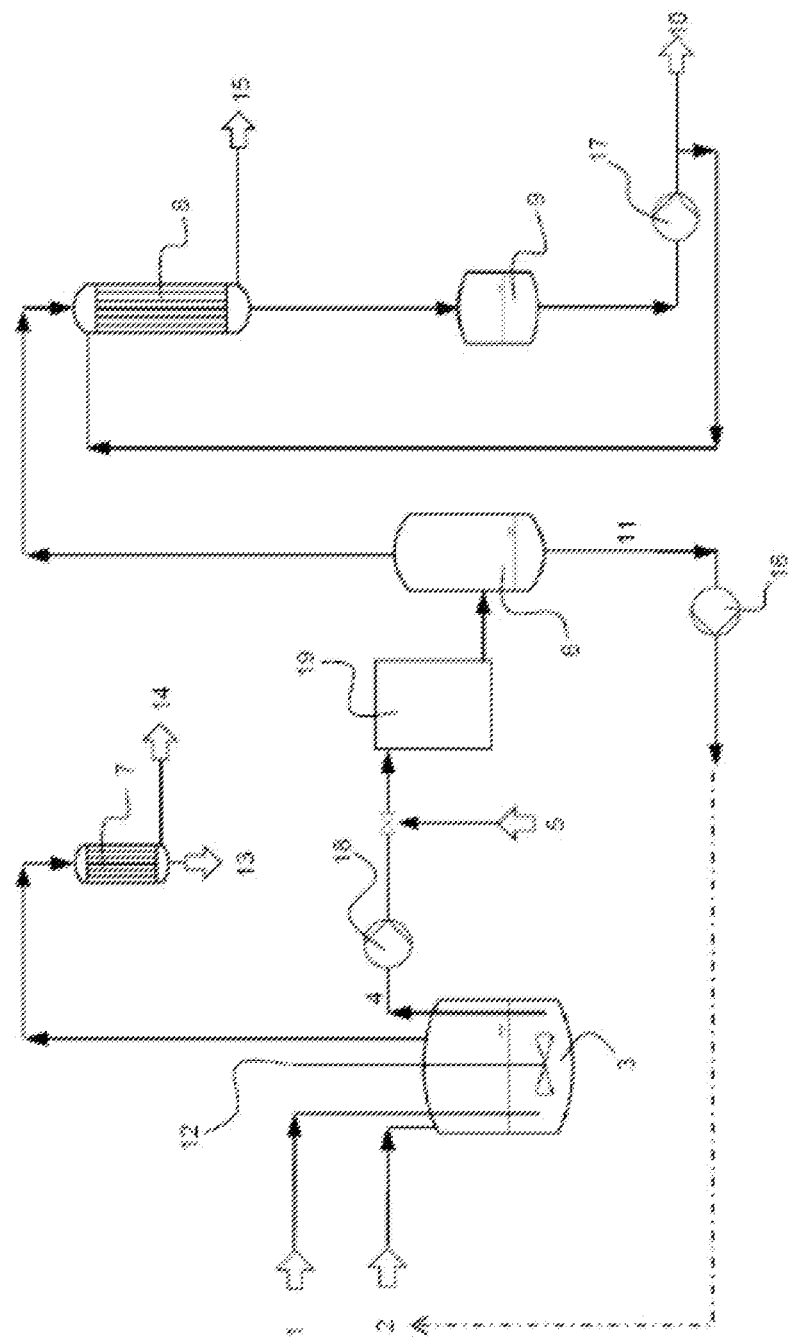

This application claims the benefit of European Patent Application No. 13171627.6, filed Jun. 12, 2013.

The present invention relates to a process for the preparation of 5-hydroxymethylfurfural (HMF), which comprises the following steps:
provision or preparation of a starting mixture, comprising
one, two or more starting compounds selected from the group consisting of hexoses, oligosaccharides comprising hexose units, and polysaccharides comprising hexose units,
one, two or more organic salts with a melting point <180° C. and a boiling point >200° C. at 1013.25 hPa,
optionally additionally one or more catalysts for the conversion of the one starting compound or at least one of the two or more starting compounds to 5-hydroxymethylfurfural (HMF),
optionally water,
optionally further substances,
adjustment of reaction conditions such that an amount of the starting compound or starting compounds converts to HMF.

Processes of this type are known for example from CN 102399203 and Wei et al. in Green Chem. 2012, 14, pages 1220-1226. These documents disclose a distillative process for the simultaneous preparation and isolation of HMF by degradation of fructose and glucose in ionic liquids. The process comprises the addition of a saccharide to an ionic liquid based on imidazolium derivatives, preferably imidazolium derivatives with long alkyl side chains (e.g. 1-methyl-3-octylimidazolium chloride) in the presence of a cocatalyst and a stripping agent at 100 to 500 Pa, a reaction temperature of 120-180° C. and a reaction time of 10 to 60 minutes. The stripping agent is nitrogen, another inert gas, carbon dioxide, a C1-C8 alkane, acetone or methyl isobutyl ketone.

Numerous other processes for the preparation of HMF from hexoses, oligosaccharides and polysaccharides are also known. HMF is usually prepared in this connection by acid-catalyzed dehydration of hexoses such as glucose or fructose. The reaction product obtained is acidic solutions which, besides the HMF, comprises unreacted starting materials and/or byproducts. During the HMF synthesis, only a partial conversion of the starting materials (starting compounds) generally takes place in order to avoid the formation of byproducts. In general, the resulting solutions therefore comprise unreacted starting compounds or oligomers or polymers composed of hexoses. At higher conversions, the amount of undesired byproducts usually increases.

The separating off of the HMF from the product mixture, which also comprises starting materials or byproducts of the HMF synthesis besides HMF, is regularly particularly complex and hinders the preparation of pure HMF.

Feroz Kabir Kazi et al. discloses in Chem Eng. J. 2011, 169, pages 329-338 the separation off of HMF from an acidic reaction solution by means of a complex extraction process using an organic solvent (butanol); a solution of HMF in butanol is obtained.

DE-A 3601281 discloses a chromatographic separation process in which firstly organic solvents are removed and then the aqueous HMF solution is separated off with an ion exchanger column. The resulting HMF fraction is crystallized.

A further method of separating off HMF from the reaction solution or the product mixture is the conversion of HMF to another compound that is easier to separate off, optionally followed by a back-conversion to HMF after separation has taken place. For example, according to Mark Mascal and Edward B. Nikitin in Angew. Chemie 2008, 47, pages 7924-7926, HMF is converted to the more stable 5-chloromethylfurfural and then converted again to HMF or derivatives thereof. Alternatively, according to EP-A 1834950, the ethers, or according to EP-A 1834951, the esters, of HMF are prepared which, after separation has taken place, are directly suitable for further syntheses.

Haru Kawamoto, Shinya Saito et al. describe in J. Wood Sci. (2007), 53, pages 127-133 the pyrolysis of cellulose with the formation of levoglucosenone, furfural and/or HMF under various conditions, including with the introduction of steam.

FR 2663933 and FR 2664273 disclose how fructose and sucrose are converted to HMF in a melt of acidic salts ($Na_3PO_4$ and $KHSO_4$) under the action of superheated steam. A small fraction of the HMF here is entrained by the steam, but the majority of the HMF is then isolated from the salt melt by means of extraction.

U.S. Pat. No. 4,400,468 discloses the acidic hydrolysis of biomass under the action of steam to give sugars and the direct conversion of the hexose fractions present in the mixture to HMF. In this case, however, the HMF formed is not isolated in pure form.

However, HMF should be in the purest possible form for subsequent syntheses. Of suitability for such subsequent syntheses are in particular aqueous solutions of HMF which comprise byproducts or residual starting materials at most in very small amounts, if at all. Processes known hitherto for preparing HMF or aqueous solutions thereof with adequate purity are extremely complex.

To prepare 5-hydroxymethylfurfural (HMF) from one or more starting compounds selected from the group consisting of hexoses, oligosaccharides comprising hexose units, and polysaccharides comprising hexose units, catalysts are usually used. catalysts which catalyze the direct conversion of a starting compound to HMF as well as catalysts which catalyze the conversion of a starting compound to an intermediate product which is formed from the starting compound during the preparation of HMF, as well as finally also catalysts which catalyze the conversion of such an intermediate product to a consecutive intermediate product or to HMF are in the following text generally considered to be catalysts for the conversion of the starting compound(s) to 5-hydroxymethylfurfural (HMF). In processes for the preparation of HMF from said starting compounds, more than just one catalyst is often used. A catalyst used often also has one or more further functions. For example, in the prior art use is often made in processes for the preparation of HMF from hexoses, corresponding oligosaccharides and/or corresponding polysaccharides of metal salts or metal oxides which, on the one hand, serve for the stabilization of the HMF formed, but, on the other hand, also as catalyst for the isomerization of glucose to fructose. The catalysts known from the prior art can also be used for the purposes of the present invention. An isomerization with metal salts is disclosed for example in the following documents: Glucose-Isomerization with Chromium-salts—Science 2007, 316, 1597-1600; Angew. Chem. Int. Ed. 2008, 47, 9345-9348; Chem. Eur. J. 2011, 17, 5281-5288; Glucose-Isomerization with rare-earth metals—J. Mol. Cat. A 2012, 356, 158-164; HMF from glucose with lanthanides—Green Chem. 2010, 12, 321-325; Conversion of Cellulose to Furans with metal salts—J. Mol. Catal. A 2012, 357, 11-18; Sn-Beta zeolitess—ACS Catal. 2011, 1, 408-410.

As regards the use of ionic liquids, two documents have already been mentioned above. Such a use of ionic liquids, in particular of substituted imidazolium chloride derivatives, for the synthesis of HMF from fructose and glucose has also otherwise been well described in the literature. However, not only is the isolation of the HMF formed from the ionic liquid regularly very complex—in most cases the ionic liquid is extracted with an organic solvent—but usually the conversion of the starting compounds also proceeds comparatively poorly in the presence of water in ionic liquids. Consequently, in the prior art value is placed on converting the starting compound used (e.g. the saccharide used) in an extremely anhydrous ionic liquid. Consequently, the ionic liquid must be dewatered prior to use in a laborious manner (cf. e.g. Biores. Tech. 2011, 102, 4179-4183).

The negative influence of water in the reaction medium during the conversion of sugars, in particular fructose and glucose, to HMF has been well described in the literature (e.g. Carbohydr. Res. 1977, 54, 177-183; Science 2007, 136, 1597-1600). As is well known to the person skilled in the art, water on the one hand slows the dehydration reaction of the sugars and on the other hand promotes the rehydration and cleavage of the HMF formed into formic acid and levulinic acid (for the postulated mechanism of the reaction see Science 2006, 312, 1933-1937).

It was a primary object of the present invention to indicate a process for the preparation of HMF which can be utilized in large-scale plants and with which HMF is prepared in a simple and effective manner. The HMF here should be obtained in the purest possible form with high yields (based on the amount of starting compounds used). Moreover, the HMF prepared should be separated off or readily separable from unreacted starting compounds as well as byproducts.

In industrial processes, the conversion should be carried out in a technically and economically advantageous temperature and pressure range with high conversion and high space-time yield. The process indicated should permit the use of commercially available aqueous saccharide solutions in different concentrations and/or make it easier compared with processes from the prior art. The indicated process should, however, preferably also be able to be used for the conversion of crystalline saccharides and crystalline pure hexoses. The process according to the invention should preferably be suitable for preventing or limiting so-called fouling, i.e. the undesired conversion of sugars used to caramelization products and other byproducts; in processes from the prior art fouling regularly leads to soilings and contaminations of the reactor and thus hinders the implementation and control of the conversion reactions.

This object is achieved according to the invention by a process for the preparation of 5-hydroxymethylfurfural (HMF), having the following steps:

provision or preparation of a starting mixture, comprising
one, two or more starting compounds selected from the group consisting of hexoses, oligosaccharides comprising hexose units, and polysaccharides comprising hexose units,
one, two or more organic salts with a melting point <180° C. and a boiling point >200° C. at 1013.25 hPa,
optionally additionally one or more catalysts for the conversion of the one starting compound or at least one of the two or more starting compounds to 5-hydroxymethylfurfural (HMF),
optionally water,
optionally further substances, adjustment of first reaction conditions in the starting mixture, such that a first amount of the one starting compound or at least one of the two or more starting compounds converts to HMF and thus forms an intermediate product mixture, where the temperature under the first reaction conditions is in the range from 100 to 160° C.

adjustment of second reaction conditions in a mixture which comprises the intermediate product mixture or a fraction of the intermediate product mixture, such that an amount of the intermediate product mixture converts to HMF and thus forms a product mixture, where the temperature under the second reaction conditions is in the range from 165 to 250° C., with HMF being separated off from the product mixture during this conversion.

In the process according to the invention, a starting mixture is thus firstly provided or prepared. The starting mixture comprises one, two or more starting compounds selected from the group consisting of hexoses, oligosaccharides comprising hexose units, and polysaccharides comprising hexose units. The hexoses used are preferably fructose, glucose and mixtures thereof. They are particularly preferably fructose or mixtures of fructose with glucose. Very particular preference is given to the use of fructose. The polysaccharide used is preferably cellulose or starch. The oligosaccharides used are preferably degradation products of cellulose or starch. The use of other polysaccharides comprising hexose units or oligosaccharides comprising hexose units, however, may be preferred in individual cases. Usually, preference is given to the use of polysaccharides or oligosaccharides which are built up of hexose units (and thus in particular comprise no pentose units), although in individual cases the use of polysaccharides or oligosaccharides which comprise both hexose units and also pentose units may also be advantageous.

In the present text, the term "hexose" is understood as meaning monosaccharide whose carbon backbone comprises six carbon atoms. In particular, the term "hexose" comprises aldohexoses such as e.g. glucose, galactose and mannose, as well as ketohexoses (hexuloses) such as e.g. fructose and sorbose.

The starting mixture provided or prepared in the process according to the invention comprises, besides the starting compound or compounds, in each case one, two or more organic salts with a melting point <180° C. and a boiling point >200° C. at 1013.25 hPa. Such organic salts are often referred to in the literature as "ionic liquids". According to the invention, preference is given to a process where said organic salt or one, two or all of said one, two or more organic salts with a melting point <180° C. and a boiling point >200° C. at 1013.25 hPa is or are selected from the group of the salts with a boiling point >250° C., preferably >300° C., at 1013.25 hPa and/or is or are selected from the group of the salts with a melting point <150° C., preferably <120° C., preferably <100° C., at 1013.25 hPa.

Ionic liquids which are already present at room temperature in the liquid state are described for example by K. N. Marsh et al., Fluid Phase Equilibria 2004, 219, 93-98 and J. G. Huddleston et al., Green Chemistry 2001, 3, 156-164.

Ionic liquids suitable for use in the process according to the invention are also described in WO 2008/090155 (p. 4, line 38 to p. 37, line 31) and WO 2008/090156 (p. 7, line 1 to p. 39, line 37), to which reference is hereby made.

Cations as well as anions are present in the ionic liquid. In some cases, within the ionic liquid, from the cation a proton or an alkyl radical can be transferred to the anion, the result of which is two neutral molecules. In the ionic liquid used according to the invention, an equilibrium of anions, cations as well as neutral molecules formed therefrom can thus be present.

Preferred ionic liquids for use in processes according to the invention are combinations of nitrogen-containing cation components (such as imidazolium derivatives) with anion components, where the anions are preferably halogen ions or anions of strong acids (such as methanesulfonate, p-toluenesulfonate, hydrogen sulfate, etc.).

Suitable compounds which are suitable for the formation of the cation of ionic liquids which are to be used in a process according to the invention are described e.g. in DE 102 02 838 A1 ([0030] to [0073]). These compounds comprise preferably at least one heteroatom, such as e.g. 1 to 10 heteroatoms, which are preferably selected from nitrogen, oxygen, phosphorus and sulfur atoms. Preference is given to compounds which comprise at least one nitrogen atom and optionally additionally at least one further heteroatom different from nitrogen. Preference is given to compounds which comprise at least one nitrogen atom, particularly preferably 1 to 10 nitrogen atoms, in particular 1 to 5 nitrogen atoms, very particularly preferably 1 to 3 nitrogen atoms and specifically 1 or 2 nitrogen atoms. The last-mentioned nitrogen compounds can comprise further heteroatoms such as oxygen, sulfur or phosphorus atoms.

Preference is given to those compounds which comprise at least one five- to six-membered heterocycle, in particular a five-membered heterocycle, which has at least one nitrogen atom, and optionally one oxygen or sulfur atom. Particular preference is given to those compounds which comprise at least one five- to six-membered heterocycle which has one, two or three nitrogen atoms and a sulfur atom or an oxygen atom, very particular preference being given to those with two nitrogen atoms. Furthermore, preference is given to aromatic heterocycles.

Preferred cations of ionic liquids (i.e. organic salts with a melting point <180° C. and a boiling point >200° C. at 1013.25 hPa) for use in a process according to the invention are unsubstituted or substituted imidazolium ions. Particularly suitable imidazolium ions are 1-methylimidazolium, 1-ethylimidazolium, 1-(1-propyl)imidazolium, 1-(1-allyl)imidazolium, 1-(1-butyl)imidazolium, 1-(1-octyl)imidazolium, 1-(1-dodecyl)imidazolium, 1-(1-tetradecyl)imidazolium, 1-(1-hexadecyl)imidazolium, 1,3-dimethylimidazolium, 1,3-diethylimidazolium, 1-ethyl-3-methylimidazolium, 1-(1-butyl)-3-methylimidazolium1-(1-butyl)-3-ethylimidazolium, 1-(1-hexyl)-3-methylimidazolium, 1-(1-hexyl)-3-ethylimidazolium, 1-(1-hexyl)-3-butylimidazolium, 1-(1-octyl)-3-methylimidazolium, 1-(1-octyl)-3-ethylimidazolium, 1-(1-octyl)-3-butylimidazolium, 1-(1-dodecyl)-3-methylimidazolium, 1-(1-dodecyl)-3-ethylimidazolium, 1-(1-dodecyl)-3-butylimidazolium, 1-(1-dodecyl)-3-octylimidazolium, 1-(1-tetradecyl)-3-methylimidazolium, 1-(1-tetradecyl)-3-ethylimidazolium, 1-(1-tetradecyl)-3-butylimidazolium, 1-(1-tetradecyl)-3-octylimidazolium, 1-(1-hexadecyl)-3-methylimidazolium, 1-(1-hexadecyl)-3-ethylimidazolium, 1-(1-hexadecyl)-3-butylimidazolium, 1-(1-hexadecyl)-3-octylimidazolium, 1,2-dimethylimidazolium, 1,2,3-trimethylimidazolium, 1-ethyl-2,3-dimethylimidazolium, 1-(1-butyl)-2,3-dimethylimidazolium, 1-(1-hexyl)-2,3-dimethylimidazolium, 1-(1-octyl)-2,3-dimethylimidazolium, 1,4-dimethylimidazolium, 1,3,4-trimethylimidazolium, 1,4-dimethyl-3-ethylimidazolium, 3-methylimidazolium, 3-ethylimidazolium, 3-n-propylimidazolium, 3-n-butylimidazolium, 1,4-dimethyl-3-octylimidazolium, 1,4,5-trimethylimidazolium, 1,3,4,5-tetramethylimidazolium, 1,4,5-trimethyl-3-ethylimidazolium, 1,4,5-trimethyl-3-butylimidazolium, 1,4,5-trimethyl-3-octylimidazolium, 1-prop-1-en-3-yl-3-methylimidazolium and 1-prop-1-en-3-yl-3-butylimidazolium. Specifically suitable imidazolium ions (IVe) are 1,3-diethylimidazolium, 1-ethyl-3-methylimidazolium, 1-(n-butyl)-3-methylimidazolium.

The anion of an ionic liquid for use in a process according to the invention is preferably selected from 1) Anions of the formulae: $F^-$, $Cl^-$, $Br^-$, $I^-$, $BF_4^-$, $PF_6^-$, $CF_3SO_3^-$, $(CF_3SO_3)_2N^-$, $CF_3CO_2^-$, $CCl_3CO_2^-$, $CN^-$, $SCN^-$, $OCN^-$.

2) Anions of the formulae: $SO_4^{2-}$, $HSO_4^-$, $SO_3^{2-}$, $HSO_3^-$, $R^cOSO_3^-$, $R^cSO_3^-$.

3) Anions of the formulae: $PO_4^{3-}$, $HPO_4^{2-}$, $H_2PO_4^-$, $R^cPO_4^{2-}$, $HR^cPO_4^-$, $R^cR^dPO_4^-$.

4) Anions of the formulae: $R^cHPO_3^-$, $R^cR^dPO_2^-$, $R^cR^dPO_3^-$.

5) Anions of the formulae: $PO_3^{3-}$, $HPO_3^{2-}$, $H_2PO_3^-$, $R^cPO_3^{2-}$, $R^cHPO_3^-$, $R^cR^dPO_3^-$.

6) Anions of the formulae: $R^cR^dPO_2^-$, $R^cHPO_2^-$, $R^cR^dPO^-$, $R^cHPO^-$.

7) Anions of the formula: $R^cCOO^-$.

8) Anions of the formulae: $BO_3^{3-}$, $HBO_3^{2-}$, $H_2BO_3^-$, $R^cR^dBO_3^-$, $R^cHBO_3^-$, $R^cBO_3^{2-}$, $B(OR^c)(OR^d)(OR^e)(OR^f)^-$, $B(HSO_4)_4^-$, $B(R^cSO_4)_4^-$.

9) Anions of the formulae: $R^cBO_2^{2-}$, $R^cR^dBO^-$.

10) Anions of the formulae: $HCO_3^-$, $CO_3^{2-}$, $R^cCO_3^-$.

11) Anions of the formulae: $SiO_4^{4-}$, $HSiO_4^{3-}$, $H_2SiO_4^{2-}$, $H_3SiO_4^-$, $R^cSiO_4^{3-}$, $R^cR^dSiO_4^{2-}$, $R^cR^dR^eSiO_4^-$, $HR^cSiO_4^{2-}$, $H_2R^cSiO_4^-$, $HR^cR^dSiO_4^-$.

12) Anions of the formulae: $R^cSiO_3^{3-}$, $R^cR^dSiO_2^{2-}$, $R^cR^dR^eSiO^-$, $R^cR^dR^eSiO_3^-$, $R^cR^dR^eSiO_2^-$, $R^cR^dSiO_3^{2-}$.

13) Anions of the formulae:

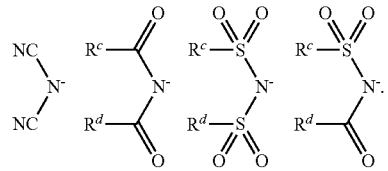

14) Anions of the formulae:

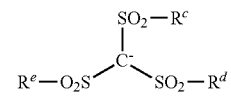

15) Anions of the formula: $R^cO^-$.

16) Anions of the formulae: $HS^-$, $[S_v]^{2-}$, $[HS_v]^-$, $[R^cS]^-$, where v is a positive integer from 2 to 10.

The radicals $R^c$, $R^d$, $R^e$ and $R^f$, preferably independently of one another, are hydrogen;

unsubstituted or substituted alkyl, preferably unsubstituted or substituted C1-C30-alkyl, particularly preferably unsubstituted or substituted C1-C18-alkyl, which may be interrupted by at least one heteroatom or heteroatom-containing group;

unsubstituted or substituted aryl, preferably unsubstituted or substituted C6-C14-aryl, particularly preferably unsubstituted or substituted C6-C10-aryl;

unsubstituted or substituted cycloalkyl, preferably unsubstituted or substituted C5-C12-cycloalkyl;

unsubstituted or substituted heterocycloalkyl, preferably unsubstituted or substituted heterocycloalkyl with 5 or 6 ring atoms, where the ring has 1, 2 or 3 heteroatoms or heteroatom-containing groups besides carbon ring atoms;

unsubstituted or substituted heteroaryl, preferably unsubstituted or substituted heteroaryl with 5 to 10 ring atoms, where the ring has 1, 2 or 3 heteroatoms or heteroatom-containing groups besides carbon ring atoms, these being selected from oxygen, nitrogen, sulfur and $NR^a$; where in anions which have a plurality of radicals $R^c$ to $R^f$, also in each case two of these radicals together with part of the anion to which they are bonded, can be at least one saturated, unsaturated or aromatic ring or a ring system with 1 to 12 carbon atoms, where the ring or the ring system can have 1 to 5 nonadjacent heteroatoms or heteroatom-containing groups which are preferably selected from oxygen, nitrogen, sulfur and NRa, and where the ring or the ring system is unsubstituted or can be substituted.

Preferred anions are $Cl^-$, $Br^-$, formate, acetate, propionate, butyrate, lactate, saccharinate, carbonate, hydrogencarbonate, sulfate, sulfite, C1-C4-alkylsulfates, methanesulfonate, tosylate, trifluoroacetate, C1-C4-dialkylphosphates and hydrogensulfate.

Particularly preferred anions are $Cl^-$, $Br^-$, $HCOO^-$, $CH_3COO^-$, $CH_3CH_2COO^-$, carbonate, hydrogencarbonate, sulfate, sulfite, tosylate, $CH_3SO_3^-$ or $CH_3OSO_3^-$.

The anions are very particularly preferably selected from $Cl^-$ and $CH_3SO_3^-$ (methanesulfonate).

Suitable ionic liquids for use in the process according to the invention are commercially available, e.g. under the trade name Basionic® from BASF SE.

Imidazolium chlorides or imidazolium methanesulfonates or mixtures thereof are advantageous for use in the process according to the invention.

Furthermore advantageous for use in the process according to the invention are e.g.: 1-ethyl-3-methylimidazolium chloride (EMIM Cl, Basionic ST 80), 1-ethyl-3-methylimidazolium methanesulfonate (EMIM $CH_3SO_3$, Basionic ST 35), 1-butyl-3-methylimidazolium chloride (BMIM Cl, Basionic ST 70), 1-butyl-3-methylimidazolium methanesulfonate (BMIM $CH_3SO_3$, Basionic ST 78), methylimidazolium chloride (HMIM Cl, Basionic AC 75), methylimidazolium hydrogensulfate (HMIM $HSO_4$ Basionic AC 39), 1-ethyl-3-methylimidazolium hydrogensulfate (EMIM $HSO_4$ Basionic AC 25), 1-butyl-3-methylimidazolium hydrogensulfate (BMIM $HSO_4$ Basionic AC 28), 1-ethyl-3-methylimidazolium acetate (EMIM Acetate, Basionic BC 01), 1-butyl-3-methylimidazolium acetate (BMIM Acetate, Basionic BC 02).

Particular preference is given to 1-ethyl-3-methylimidazolium chloride, 1-butyl-3-methylimidazolium chloride, methylimidazolium chloride, 1-ethyl-3-methylimidazolium methanesulfonate, 1-butyl-3-methylimidazolium methanesulfonate and mixtures thereof.

Very particular preference is given to 1-ethyl-3-methylimidazolium chloride (EMIM Cl, Basionic ST 80), 1-butyl-3-methylimidazolium chloride (BMIM Cl, Basionic ST 70) and 1-ethyl-3-methylimidazolium methanesulfonate (EMIM $CH_3SO_3$, Basionic ST 35).

In the process according to the invention, the provided or prepared starting mixture optionally additionally comprises one or more catalysts for the conversion of the one starting compound or at least one of the two or more starting compounds to 5-hydroxymethylfurfural (HMF). In a large number of application cases, the presence of one or more such additional catalysts is preferred. Preference is given in particular to the presence of a catalyst which catalyzes the conversion of fructose to HMF. When using starting compounds which comprise glucose or glucose units, preference is given to the presence of a catalyst which catalyzes the isomerization of glucose to fructose.

The catalyst used for the conversion of fructose to HMF in processes according to the invention is preferably acids. Preferred acids are present in dispersed or dissolved form in the starting mixture. Preference is given to acids dissolved in the starting mixture, preferably dissolved acids with a boiling point >200° C. at 1013.25 hPa.

The acids dissolved in the starting mixture used in a process according to the invention are inorganic or organic acids. Particular preference is given to using protic acids. By way of example, mention may be made of para-toluenesulfonic acid, methanesulfonic acid ($CH_3SO_3H$), oxalic acid, sulfuric acid, hydrochloric acid or phosphoric acid. Among the dissolved protic acids, preference is in turn given to those acids which have a boiling point >200° C. at 1013.25 hPa. Particular preference for this reason is given to the use of methanesulfonic acid.

If the starting mixture comprises a dissolved acid as catalyst, the total amount of dissolved acid in the starting mixture is preferably in the range from 0.1 to 10 mol %, particularly preferably from 0.1 to 5 mol % (based on the molar amount of hexoses and hexose units used).

Preferred catalysts for the isomerization of glucose to fructose are metal salts. Advantageously, metal chlorides or metal nitrates of the general formula $MX_n$ are used as isomerization catalyst, where M is a metal, X is chlorine or nitrate and n is an integer from 1 to 4. These isomerization catalysts are preferably then present in the starting mixture if the starting mixture comprises glucose and/or glucose units, as for example in the case of using sucrose. The use of isomerization catalysts has already been described in the literature (Science 2007, 316, 1597-1600, Carbohydr. Pol. 2012, 90, 792-798, Chem. Eur. J. 2011, 17, 5281-5288, Green Chem. 2009, 11, 1746-1749). In processes according to the invention, preference is given to using metal chlorides or metal nitrates selected from the group $CrCl_2$, $CrCl_3$, $AlCl_3$, $FeCl_2$, $FeCl_3$, CuCl, $CuCl_2$, CuBr, $VCl_3$, $MoCl_3$, $PdCl_2$, $PtCl_2$, $RuCl_3$, $RhCl_3$, $Ni(NO_3)_2$, $Co(NO_3)_2$, $Cr(NO_3)_3$, $SnCl_4$. Particular preference is given to $CrCl_2$ and $CrCl_3$. The use of $IrCl_3$ is also advantageous. Alternatively or additionally, in processes according to the invention preference is given to using metal salts whose cation is preferably selected from the group consisting of Cr, Al, Fe, Cu, V, Mo, Pd, Pt, Ru, Rh, In, Ni, Co and Sn and/or whose anion is selected from the group consisting of $Cl^-$, $Br^-$, formate, acetate, propionate, butyrate, lactate, saccharinate, carbonate, hydrogencarbonate, sulfate, sulfite, C1-C4-alkylsulfates, $CH_3SO_3^-$ (methanesulfonate), tosylate, trifluoroacetate, C1-C4-dialkylphosphates and hydrogensulfate. Particularly preferred anions are $Cl^-$, $Br^-$, $HCOO^-$, $CH_3COO^-$, $CH_3CH_2COO^-$, carbonate, hydrogencarbonate, sulfate, sulfite, tosylate, $CH_3SO_3^-$ or $CH_3OSO_3^-$. Very particularly preferably, the anions are selected from $Cl^-$ and $CH_3SO_3^-$. Preference is given to using metal salts whose anion is identical to the anion of the, or at least of one of the, organic salts with a melting point <180° C. and a boiling point >200° C. at 1013.25 hPa (ionic liquid). In this way, anion exchange is avoided; preference is given to the use of Cr(III) methanesulfonate (when simultaneously using an ionic liquid with methanesulfonate as anion).

Alternatively or additionally, metal oxides, ion exchange resins and zeolites can be used as catalyst in a process according to the invention.

The organic salts used in the context of the present invention and having a melting point <180° C. and a boiling point >200° C. at 1013.25 hPa (ionic liquids) usually likewise have a catalytic effect. In the present case, however, for the purposes of a quantitative consideration of the composition of a starting mixture to be provided or prepared these organic salts are not considered to be catalysts, but are considered separately.

In a process according to the invention for the preparation of HMF, the provided or prepared starting mixture optionally comprises water. Advantageously, the starting mixture comprises water in an amount of less than 50% by weight, based on the total amount of the provided or prepared starting mixture. Preferably, the fraction of water is in the range from 1 to 50% by weight, preferably 1 to 30% by weight, based on the total amount of the provided or prepared starting mixture.

Preferably, in a process according to the invention for the purpose of preparing a starting mixture, an aqueous mixture comprising one, two or more starting compounds selected from the group consisting of hexoses, oligosaccharides comprising hexose units, and polysaccharides comprising hexose units, is mixed with the further constituents of the starting mixture to be prepared, i.e. in particular with the organic salts and optionally the catalysts and further substances. Before, during or after adjusting the first reaction conditions in the starting mixture, water is then separated off, preferably continuously, from the aqueous mixture of the starting compounds or from the starting mixture preferably at a pressure in the range from 50 to 300 mbar. In this way, a detectable impairment of the dehydration of the hexose used or of the hexose units of the oligosaccharides or polysaccharides used is avoided.

Preferably, in a process according to the invention for the preparation of the starting mixture, an aqueous solution of the starting compounds is introduced into a distillation or evaporation vessel such that at least some of the introduced water evaporates upon combining with the other constituents of the starting mixture. For this, the temperature within the distillation or evaporation vessel is typically adjusted to a value >100° C. and/or the pressure within said vessel is adjusted to a value in the range from 50 to 300 mbar.

According to a preferred embodiment of the process according to the invention, the starting mixture is prepared by the following steps:

An aqueous (pre)mixture comprising one, two or more starting compounds selected from the group consisting of hexoses, oligosaccharides comprising hexose units, and polysaccharides comprising hexose units is provided. Spatially separate therefrom, a (pre)mixture of further constituents of the starting mixture is provided. Directly prior to adjusting the first reaction conditions, the provided (pre)mixtures are combined to give the starting mixture, preferably at most 5 minutes, preferably at most 1 minute, before adjusting the first reaction conditions. The provided aqueous (pre)mixture of the starting compound or starting compounds and/or the overall mixture obtained by combining the provided (pre)mixtures is preferably subjected to a sudden pressure reduction (e.g. transition from atmospheric pressure or superatmospheric pressure to subatmospheric pressure by means of an overflow or regulating valve) and in so doing water is partially evaporated and converted to the gas phase (so-called "flashing"). Preferably, one or both (pre)mixtures are preheated prior to combining already to a temperature in the range from 25 to 120° C. If the aqueous (pre)mixture of the starting compound or of the starting compounds is preheated to such a temperature and then preferably subjected to a sudden pressure reduction, this brings about a particularly effective evaporation of a particularly large water fraction into the gas phase. A preheating of the corresponding mixture is advantageous particularly when using one or more organic salts with a melting point >25° C. This applies correspondingly for the use of organic salts with a high viscosity at 25° C. or other low processing temperatures.

If glucose, oligosaccharides comprising glucose units and polysaccharides comprising glucose units are used as starting compound in an aqueous mixture, it is advantageous to use an isomerization catalyst of the type mentioned above. Preference is given to using a metal chloride, metal nitrate or metal methanesulfonate. As regards the separate provision of the (pre)mixtures to be combined, that stated above is applicable. The isomerization catalyst is preferably initially introduced in the mixture of the organic salts.

In a process according to the invention for the preparation of HMF, a starting mixture is provided or prepared which optionally comprises further substances. These further substances are, for example, impurities. These can come from return streams of the organic salts from a previous reaction.

In the process according to the invention, first reaction conditions are adjusted in the provided or prepared starting mixture. The temperature, being a particularly relevant reaction parameter, is, in the case of the first reaction conditions, in the range from 100 to 160° C., often a temperature during the first reaction conditions in the range from 100 to 140° C. is preferred. The temperature, the further reaction conditions and the composition of the starting mixture are selected such that, in the starting mixture after adjusting the first reaction conditions, a first amount of the one starting compound or at least one of the two or more starting compounds converts to HMF and thus forms an intermediate product mixture.

The conversion of the starting compounds under the first reaction conditions in the starting mixture and the yield of HMF under the first reaction conditions can be varied by varying the reaction parameters and the composition of the starting mixture. For the purposes of the process according to the invention, it is advantageous to adjust the reaction conditions in the starting mixture such that in the resulting intermediate product mixture before adjusting the second reaction conditions at most an amount of HMF is present which corresponds to a molar yield of 55 to 80%, based on the total amount of hexoses and hexose units used in the starting mixture. If hexoses on the one hand and oligosaccharides or polysaccharides comprising hexose units on the other hand are used simultaneously and together in the process according to the invention, the total amount of hexoses and hexose units is composed from the sum of the individual quantitative amounts. Each hexose unit of an oligosaccharide or polysaccharide thus likewise contributes as much to the total quantitative amount as an individual molecule of a hexose used. At the reaction temperature provided according to the invention (which is comparatively low compared to process embodiments from the prior art) under the first reaction conditions, comparatively small amounts of those reaction products which cannot be further converted to HMF surprisingly result. This is also applicable and particularly so when the first reaction conditions (as is preferred) are established such that said molar yield in the intermediate product mixture is in the range from 55 to 80% before adjusting the second reaction conditions. Under the preferred first reaction conditions, usually as yet unreacted amounts of the one, two or more starting compounds remain which can be reacted under the second reaction conditions. Moreover, however, those intermediate products are also present as are obtained for example by simply single or double dehydration of the hexose (or hexose units) used. Such intermediate products can also be converted to HMF (particularly under the second reaction conditions of the process according to the invention).

In a process according to the invention for the preparation of HMF, after forming an intermediate product mixture under first reaction conditions (at a temperature in the range from 100 to 160° C., preferably at a temperature in the range from 100 to 140° C.), a consecutive step is carried out under second reaction conditions. These second reaction conditions are adjusted in a mixture which comprises the intermediate product mixture or a fraction of the intermediate product mixture. This means that either the entire intermediate product mixture which has been obtained under the first reaction conditions is subjected to the second reaction conditions, or merely a quantitative fraction of the resulting intermediate product mixture. However, this also means that the mixture which is subjected to the second reaction conditions can also comprise further constituents in addition to the intermediate product mixture or the fraction of the intermediate product mixture. The second reaction conditions in the mixture, which comprises the intermediate product mixture or a fraction of the intermediate product mixture, are chosen such that an amount of the intermediate product mixture (present in the mixture) converts to HMF and a product mixture is thus formed. The temperature under the second reaction conditions is in the range from 165 to 250° C., preferably in the range from 180 to 250° C., further preferably in the range from 190 to 250° C., particularly preferably in the range from 200 to 240° C. The reaction temperature under the second reaction conditions is thus significantly higher than the reaction temperature during the first reaction conditions, preferably at least 20° C. higher. According to the invention, HMF is separated off from the product mixture during the conversion of an amount of the intermediate product mixture to HMF.

Preferably, the mixture which comprises the intermediate product mixture or a fraction of the intermediate product mixture, before or upon adjustment of the second reaction conditions, is subjected to a sudden pressure reduction (e.g. conversion from atmospheric pressure or superatmospheric pressure to subatmospheric pressure by means of an overflow or regulating valve) and in so doing the volatile constituents partially evaporate and convert to the gas phase (so-called "flashing").

Surprisingly, it has been found in our experiments that the total yield of HMF is increased by virtue of the stepwise conversion under first reaction conditions and second reaction conditions in a process according to the invention compared with process configurations in particular in which the first reaction conditions are not adjusted and the hexose-containing mixtures are exposed directly to temperatures >165° C.; this is applicable especially for implementing the process according to the invention in large-scale plants. Moreover, so-called fouling is suppressed by the process configuration according to the invention, i.e. the undesired conversion of the starting compounds used to in particular caramelization products, which soil the reactor and thus hinder the production of HMF.

During the conversion of an amount of the intermediate product mixture to HMF under the second reaction conditions in the then present mixture, HMF is separated off from the product mixture. In this connection, the customary separation processes can be used to separate off the HMF, such as, for example, the separation processes of distillation or extraction. For carrying out the process according to the invention, preference is given to a configuration in which, under the second reaction conditions, HMF is separated off from the product mixture by means of distillation, preferably by means of carrier vapor distillation. The term "carrier vapor distillation" here comprises any distillation using a carrier gas, in particular a distillation preferred here with co-effect of steam (steam distillation).

Preferably, for the separation by means of distillation, the product mixture is brought into contact in a process according to the invention under the second reaction conditions with a (carrier) gas in co-current or countercurrent.

The gas used here preferably comprises one or more compounds or consists of one or more compounds, where the one or more compounds preferably have a boiling point which is lower than 200° C. at 1013.25 hPa, and is preferably greater than 60° C. at 1013.25 hPa.

Preferably, the (carrier) gas comprises one or more compounds which are selected from the group consisting of water, alcohols, monoethers, diethers, polyethers, ketones, esters and aromatics, and which are preferably selected from the group consisting of water and alcohols, and which are particularly preferably selected from the group consisting of water, methanol and 2-butanol.

Under the second reaction conditions, HMF is formed and separated off from the product mixture in a process according to the invention. Preferably, the pressure under the second reaction conditions is below 1000 mbar, further preferably in the range from 10 to 200 mbar, preferably in the range from 10 to 100 mbar, particularly preferably in the range from 20 to 80 mbar. Consequently, vacuum conditions are adjusted which facilitate in particular the distilling off of HMF from the product mixture. Particular preference is given to a process configuration in which, during the second reaction conditions, HMF is separated off from the product mixture by means of distillation at a pressure below 1000 mbar, preferably in the range from 10 to 200 mbar, preferably in the range from 10 to 100 mbar, particularly preferably in the range from 20 to 80 mbar, preferably by means of carrier vapor distillation: the pressure here is determined in the vicinity of the vacuum pump; pressure gradients known to the person skilled in the art prevail in the reactor. As regards the preferred configuration of the distillation and the (carrier) gases to be used, that stated above applies accordingly.

The first reaction conditions and the second reaction conditions can be adjusted in a process according to the invention in succession in a single reaction vessel. However, preference is given to a process configuration according to the invention in which the starting mixture is prepared or provided in a first reactor and the first reaction conditions are adjusted in the first reactor such that the intermediate product mixture is formed, and the intermediate product mixture is transferred, completely or in part, preferably in part after separating off water, to a second reactor, the second reaction conditions are adjusted in the second reactor. The second reactor here is preferably a reactive distillation device or a constituent of a reactive distillation device. For particular embodiments of this preferred process configuration, we refer to the explanations below and the description of the figures as well as the examples.

For the process configuration just explained with a first reactor and a second reactor, a configuration is advantageous in which the intermediate product mixture or parts (fraction) thereof to be transferred to the second reactor is or are subjected, before or upon entry into the second reactor, to the conditions of a distillation, preferably a flash distillation, during which HMF is separated off. Additionally or alternatively, the reactive distillation device to be used with preference has an overflow valve for generating a flash vacuum effect.

If the intermediate product mixture (or parts thereof to be transferred to the second reactor) is also subjected, prior to entry into the second reactor, to the conditions of a distillation, then this distillation is often carried out by means of a distillation device which is arranged on the first reactor. Water can be separated off from this mixture by means of the same distillation device even upon the introduction of an aqueous mixture of the starting compounds. In this connection, it is to be observed that a distillation device which is arranged on the first reactor in many cases separates off primarily water from the intermediate product mixture or an aqueous mixture of starting compounds used and separates off HMF only in small amounts; this is even desired in many cases. In many cases, therefore, preference is given to a process configuration in which the intermediate product mixture is removed in liquid form from the first reactor, and a corresponding mixture, which comprises the intermediate product mixture or a fraction of the intermediate product mixture, is subjected, in liquid form prior to or upon entry into the second reactor, to the conditions of a distillation, during which the majority of the HMF is separated off. The mixture, which comprises the intermediate product mixture or a fraction of the intermediate product mixture, here is preferably already low in water, i.e. any water introduced into the first reactor is preferably already removed from the first reactor by means of a first upstream distillation.

Preference is given to processes according to the invention in which a first and a second reactor are used (as explained above) and where the second reactor is a reactive distillation device or is a constituent of a reactive distillation device, where the reactive distillation device has an overflow valve for generating a flash vacuum effect.

The process according to the invention can be carried out continuously, semicontinuously or discontinuously.

Preferably, at least the provision or preparation of the starting mixture and the conversion to the intermediate product mixture takes place in a continuous process. In a process according to the invention in which a first reactor and a second reactor are used (as explained above), it is particularly advantageous to carry out the conversion to the intermediate product mixture continuously in the first reactor. Preferably, in such a configuration, water is likewise continuously separated off from the first reactor, preferably in the manner explained above by means of distillation. Preferably, in such configurations, the (liquid) intermediate product mixture is discharged continuously from the first reactor in the direction of the second reactor.

In processes according to the invention, the conversion of the mixture which comprises the intermediate product mixture or a fraction of the intermediate product mixture to the product mixture preferably takes place in a continuous, semicontinuous or discontinuous process, but is preferably also a continuous process in this regard; the conversion takes place preferably in the manner described above in a second reactor. In a process according to the invention, the residue of the reaction of the intermediate product mixture to the product mixture present after separating off HMF is preferably completely or partly recycled and in so doing used for preparing the starting mixture. Preferably, the residue is recycled after separating off byproducts, i.e. partially.

As already explained above, the first reaction conditions in a process according to the invention are preferably adjusted such that in the intermediate product mixture before adjusting the second reaction conditions at most an amount of HMF is present which corresponds to a molar yield of 55 to 80%, based on the amount of hexoses or hexose units used in the starting mixture. It goes without saying here that the second reaction conditions are then adjusted in a mixture which comprises the intermediate product mixture or a fraction of the intermediate product mixture. If the process according to the invention is carried out with a first reactor and a second reactor (as explained above), the intermediate product mixture is present in the first reactor. Upon transporting the preferably liquid intermediate product mixture in the direction of the second reactor, however, fractions of the intermediate product mixture can then be removed and/or the intermediate product mixture or its remaining fractions can be mixed with other substances. This results in said mixture, which comprises the intermediate product mixture or a fraction of the intermediate product mixture, and this mixture is then subjected to the second reaction conditions in the second reactor.

In a process according to the invention, the second reaction conditions are preferably adjusted such that the total molar yield of HMF exceeds a value of 60%, preferably a value of 75%, particularly preferably a value of 80%, based on the total amount of hexoses and hexose units used in the starting mixture, and/or that the amount of hexoses or hexose units reacted overall exceeds a value of 98 mol %, preferably a value of 99 mol %, based on the amount of hexoses or hexose units used in the starting mixture. The second reaction conditions here are always adjusted such that an amount of the intermediate product mixture converts to HMF; the total yield of HMF is thus increased under the second reaction conditions.

The process according to the invention is thus preferably carried out such that under the first reaction conditions a molar yield of HMF in the range from 55 to 80% is achieved, based on the amount of hexoses or hexose units used in the starting mixture, and that under the second reaction conditions a molar total yield of HMF is achieved which is greater than 60%. The first reaction conditions differ from the second reaction conditions in particular by virtue of the lower reaction temperature (first reaction conditions: 100 to 160° C.; second reaction conditions: 165 to 250° C.; as regards preferred temperature ranges, the above remarks are applicable). Surprisingly, as a result of the gentle first reaction conditions, the disadvantageous formation of byproducts is significantly reduced. It is advantageous to adjust the first reaction conditions in a first reactor and the second reaction conditions in a second, separate reactor. In the case of such a process configuration, both reactors used are soiled to a surprisingly slight extent; the cleaning expenditure is low.

Particular preference is given to a process according to the invention for the preparation of 5-hydroxymethylfurfural (HMF) with the following steps:

provision or preparation of a starting mixture in a first reactor, comprising one, two or more starting compounds selected from the group consisting of hexoses, oligosaccharides comprising hexose units, and polysaccharides comprising hexose units, one, two or more organic salts with a melting point <180° C. and a boiling point >200° C. at 1013.25 hPa, optionally additionally one or more catalysts for the conversion of the one starting compound or at least one of the two or more starting compounds to 5-hydroxymethylfurfural (HMF), optionally water, optionally further substances, adjustment of first reaction conditions in the starting mixture in the first reactor such that the first amount of the one starting compound or at least one of the two or more starting compounds converts to HMF and thus forms an intermediate product mixture, where the temperature under the first reaction conditions is in the range from 100 to 160° C., transfer of the intermediate product mixture completely or in part to a second reactor, so that a mixture results which comprises the intermediate product mixture or a fraction of the intermediate product mixture, adjustment of second reaction conditions in the second reactor in the mixture, so that a further amount of the intermediate product mixture converts to HMF and thus forms a product mixture, where the temperature under the second reaction conditions is in the range from 165 to 250° C., where during this conversion under the second reaction conditions HMF is separated off from the product mixture by means of carrier vapor distillation, where, for the separation by means of carrier vapor distillation, the product mixture is brought into contact under the second reaction conditions with a gas which comprises one or more compounds or consists of one or more compounds, where the one or more compounds have a boiling point which is lower than 200° C. at 1013.25 hPa.

For this preferred process, it is the case, as for all of the other process configurations of the process according to the invention which are referred to above as being preferred, that the stated process steps and measures are preferably combined with further steps and/or measures which are likewise referred to as being preferred in the present text.

As already explained, it is particularly advantageous to carry out the process according to the invention in a device or plant which comprises a first reactor and a second reactor; the second reactor here is preferably a reactive distillation device or a constituent of a reactive distillation device.

Entirely correspondingly, the present invention also relates to the use of a device comprising a first reactor and a second reactor for the preparation of 5-hydroxymethylfurfural (HMF), where the second reactor is a reactive distillation device or is a constituent of a reactive distillation device, where in the first reactor an intermediate product mixture comprising HMF is prepared, the intermediate product mixture is transferred completely or partly to the second reactor and, in the second reactor, further HMF is prepared from the intermediate product mixture or the transferred fraction of the intermediate product mixture, and this is distilled off. As already explained above in connection with the process according to the invention, it is the case here that the intermediate product mixture or its fraction can be a constituent of a mixture which also comprises further constituents; the above statements apply accordingly in this regard.

We will now turn to further specific aspects of the process according to the invention and/or of the use according to the invention:

In preferred configurations of the process according to the invention (as explained above), the HMF is separated off by means of carrier vapor distillation under the second reaction conditions (preferably in the second reactor or a device which comprises the second reactor). Here, a (carrier) gas is brought into contact with the product mixture for the purposes of separation. Preference in this regard is given to steam, alcohols such as, for example, methanol, ethanol, 2-butanol, mono-, di- and polyethers such as ethylene glycol dimethylether, diethylene glycol monomethyl ether, triethylene glycol, ketones such as 2-butanone or methyl isobutyl ketone, esters such as butyl acetate and aromatics such as toluene or xylene. Preference is given to polar-protic compounds which permit good interaction with HMF. The compounds used are particularly preferably steam, methanol and 2-butanol. Very particular preference is given to steam.

The treatment of the product mixture with the (carrier) gas preferably takes place at reduced pressure, particularly preferably at a pressure in the range from 10 to 200 mbar. Preferably, the pressure in the second reactor is 10 to 100 mbar, particularly preferably 20 to 80 mbar.

In a large number of configurations of the process according to the invention, it is not necessary to add a (carrier) gas as additional constituent to the product mixture. Rather, in such configurations the gas is produced in the form of steam from the water which has been introduced for example in the form of an aqueous solution of the starting compounds into the first reactor or which has formed as a result of dehydration of the converted fructoses. Irrespective of whether the (carrier) gas is added separately or not, certain ratios of the mass of mixture to be treated and the mass of (carrier) gas are preferred. Preference is given in particular to a mass ratio in the range from 0.2 to 4 parts by mass (carrier) gas per part by mass of product mixture; this applies particularly if the second reaction conditions are adjusted in a second reactor in which the product mixture is thus present from which HMF is to be separated off. Particularly preferably, said mass ratio is in the range from 0.3 to 2 parts by mass of (carrier) gas per part by mass of product mixture and very particularly preferably in the range from 0.3 to 1.5 parts by mass of (carrier) gas per part by mass of product mixture.

Of suitability for use as second reactor are, for example, customary evaporators which are designed (a) for the introduction of the mixture which comprises the intermediate product mixture or the fraction of the intermediate product mixture, and also if required (b) for the introduction of (carrier) gas and/or of the corresponding readily boiling compounds (as defined above). Preferably, such customary evaporators are designed for a continuous process mode. Particular preference is given to evaporators with a short average residence time which is in the range from 2 seconds to 10 minutes. Evaporators with such short average residence times ensure low thermal stressing of the formed dehydration products and therefore contribute to fouling being largely suppressed. The residence time has a major influence on the overall yield of HMF since even in the event of an already complete conversion of the starting compounds the distillation yield of HMF usually falls off considerably as a result of an increased residence time.

Preferably, the process according to the invention is carried out using a second reactor in such a way that the residence time in this second reactor is in the range from 1 to 120 seconds, particularly preferably in the range from 1 to 60 seconds, very particularly preferably in the range from 5 to 30 seconds. Suitable evaporators are in principle the devices customary for this purpose which, in the simplest case, comprise a container or tubes with heatable walls as heat transfer surfaces. These evaporators can be supplied with heat in a suitable manner externally via the walls, for example with steam.

In some cases, the use of a thin-film evaporator is advantageous as the second reactor in a process according to the invention. In thin-film evaporators, (a) the mixture which comprises the intermediate product mixture or a fraction of the intermediate product mixture, and (b) which is to be converted to the product mixture, is present as liquid film. Particular preference in this regard is given to vertical thin-film evaporators; vertical thin-film evaporators of this kind are known under apparatus names such as "Luwa" or in particular "Sambay" from Buss or Sulzer. Thin-film evaporators of this kind can be used without or with a rotating wiper blade.

Preferred vertical thin-film evaporators usually comprise a perpendicular tube with internal devices for distributing and mixing the mixture, which comprises the intermediate product mixture or a fraction of the intermediate product mixture, and external devices for heating the tube wall.

When using a thin-film evaporator as the second reactor, the mixture is preferably supplied in the upper section of the thin-film evaporator and spread as film on the heated tube wall. The compounds for forming the (carrier) gas can be supplied to the evaporator, preferably to the thin-film evaporator, together with the mixture or at any other desired position of the evaporator. The mixture and said compounds for preparing the (carrier) gas can be supplied to the evaporator in the same direction (co-current) or in the opposite direction (countercurrent).

If the (carrier) gas is to be conveyed countercurrently, the mixture is preferably supplied in the upper part of the evaporator and the (carrier) gas or the corresponding liquid compounds in the lower section of the evaporator. The (carrier) gas and the volatile constituents of the mixture or of the product mixture are preferably discharged at the top of the evaporator and condensed (distillate). The nonvolatile constituents (residue) preferably pass through the evaporator and are separated off as liquid product (bottom; residue).

Alternatively, for converting the mixture to the product mixture and for separating off the HMF, a distillation column is used, preferably a stripping column. The stripping column preferably then consists of a perpendicular tube with external heating and a plurality of plates for the liquid-vapor equilibrium adjustment. The feed takes place in the event of such a process configuration preferably at the top of the stripping column. A drop separator (demister) is preferably assigned to a distillation column which is used as second reactor. As a result of this, a drop entrainment (which is a sign of a non-established equilibrium and simultaneously of a fluid dynamic/flow overload) is largely or completely prevented.

In the process according to the invention, HMF is separated off from the product mixture (which comprises HMF and unreacted constituents of the mixture which comprises the intermediate product mixture or the fraction of the intermediate product mixture). If the separation takes place as explained above by means of distillation, then the distillate obtained is regularly a dilute, HMF-comprising solution. Beside HMF, the distillate also regularly comprises water (in particular from the dehydration of the starting materials or from other precursors), and also in the case of the corresponding process configuration the compounds used as (carrier) gas. Preferably, the process according to the invention is configured such that the distillate comprises at least 3% by weight of HMF, preferably at least 4% by weight of HMF and very particularly preferably at least 6% by weight of HMF, based on the total weight of the distillate. Byproducts which are formed during the conversion of the starting compounds or of the compounds that can be converted to HMF (intermediate products) of the intermediate product mixture to HMF are in particular humins (oligomers of HMF). Humins are produced in processes according to the invention when using a second reactor, which is also used for separating off HMF by means of distillation from the product mixture, usually not at all or only in very small amounts in the distillate, but for the most part in the residue (bottom). In such cases, the distillate thus usually comprises no or only very small amounts of humins; the content of humins in the distillate is preferably <2% by weight, preferably <0.5% by weight and particularly preferably <0.1% by weight, based on the total weight of the distillate. The distillate is preferably clear and has a light yellow or orange coloration (depending on the HMF content).

Usually, the distillate comprises no or only very small amounts of unreacted starting compounds. Unreacted hexoses, oligosaccharides and polysaccharides are preferably found predominantly in the bottom.

The content of unreacted starting compounds in the distillate is usually <5% by weight, preferably <2% by weight and particularly preferably <1% by weight, based on the total weight of the distillate.

It is a particular advantage of such a process according to the invention (with distillative removal of HMF from the product mixture) that byproducts of the HMF synthesis (in particular humins), the organic salts used with a melting point <180° C. and a boiling point below 200° C. at 1013.25 hPa, optionally catalysts and the unreacted starting compounds are essentially produced in the bottom.

In the process according to the invention, following separation from the product mixture, HMF is preferably obtained directly as distillate with high purity. The process according to the invention in the case of a corresponding configuration is therefore a simple and effective process for the preparation of HMF and for the simultaneous removal of HMF from byproducts and unreacted starting materials.

Such a distillate is likewise just as suitable as HMF separated off by another way as starting material for chemical syntheses. In particular, the distillate is suitable for chemical syntheses in which the starting material HMF is desired or required in high purity. By way of example, mention may be made here of the synthesis of 2,5-furandicarboxylic acid or of 2,5-bis(hydroxymethyl)furan from HMF, in which distillates of the separation of HMF from the product mixture can regularly be used without further purification steps.

In preferred configurations of the process according to the invention, a continuous distillation of volatile components is carried out, particularly under the second reaction conditions, in which HMF is separated off from the product mixture by means of distillation (preferably by means of carrier vapor distillation) and optionally using a second reactor. This is generally applicable for the present invention insofar as such a continuous distillation of volatile components preferably takes place as evaporation with one or more serially connected plates and subsequent condensation of the distillate by means of evaporators and cooling apparatuses known per se to the person skilled in the art. Examples of evaporators with one or more evaporator plates suitable in the context of the present invention are falling-film evaporators, natural circulation evaporators, forced-circulation decompression evaporators, coiled tube evaporators, thin-film evaporators and short-path evaporators. All of these types of evaporator can be used according to the invention for the continuous distillation. In the context of the present invention, particular preference is given to using evaporators which are suitable for the distillation of solids-laden liquids and have little tendency towards soiling, such as e.g. forced-circulation decompression evaporators, coiled-tube evaporators, thin-film evaporators and short-path evaporators.

The process according to the invention is preferably carried out such that, under the second reaction conditions (and thus preferably in a second reactor), HMF is separated off from the product mixture by separating a gas/liquid mixture. Such a separation of gas/liquid mixtures under the conditions of the multistage distillation can be utilized for the continuous isolation of the product of value HMF in adequate product quality and virtually without loss with virtually complete avoidance of cakings, incrustations, etc. Suitable distillation columns are in this regard e.g. stripping columns (perpendicular tube) with external heating and one or more plates (e.g. internals) for the liquid/vapor equilibrium adjustment. As regards the separation-effective internals, there are no fundamental limitations; preferably, however, arranged packings or trays are provided. The feed preferably takes place at the top of the stripping column.

In a preferred configuration of the process according to the invention, for converting the mixture which comprises the intermediate product mixture or a fraction of the intermediate product mixture, and for simultaneously separating off the gas/liquid mixture, a combination of evaporator and distillation column is used. Here, preferably both the mixture which comprises the intermediate product mixture or a fraction of the intermediate product mixture, as well as the (carrier) gas (stripping agent) are fed together in co-current to an evaporator (as regards preferred evaporators, see above) and the gas/liquid mixture emerging from the evaporator is separated in a single- or multi-plate column into a distillate stream and a bottom stream. The more readily volatile constituents are preferably discharged at the top of the column and condensed (distillate) and the less volatile constituents pass through the column and are separated off as liquid bottom product.

In an alternative embodiment of a process according to the invention, the mixture which comprises the intermediate product mixture or a fraction of the intermediate product mixture is preferably supplied to the top of a distillation column with one or more plates (stripping column). The (carrier) gas (stripping agent) is supplied to the evaporator together with the mixture (comprising the intermediate product or fraction thereof) or to any other position in the distillation column. Preferably, the (carrier) gas is supplied in the lower section of the distillation column and the distillation is operated in countercurrent mode. The more readily volatile constituents are preferably discharged at the top of the column and condensed (distillate) and the less volatile constituents pass through the column and are separated off as volatile bottom product.

Insofar as has been explained above that the (carrier) gas is passed into the evaporator at a certain position, a liquid compound can alternatively be supplied to the evaporator which only converts to the gaseous aggregate state in the evaporator and then functions as (carrier) gas (stripping agent).

The present invention is illustrated in more detail below by reference to the attached drawings and the examples.

Figure 2:
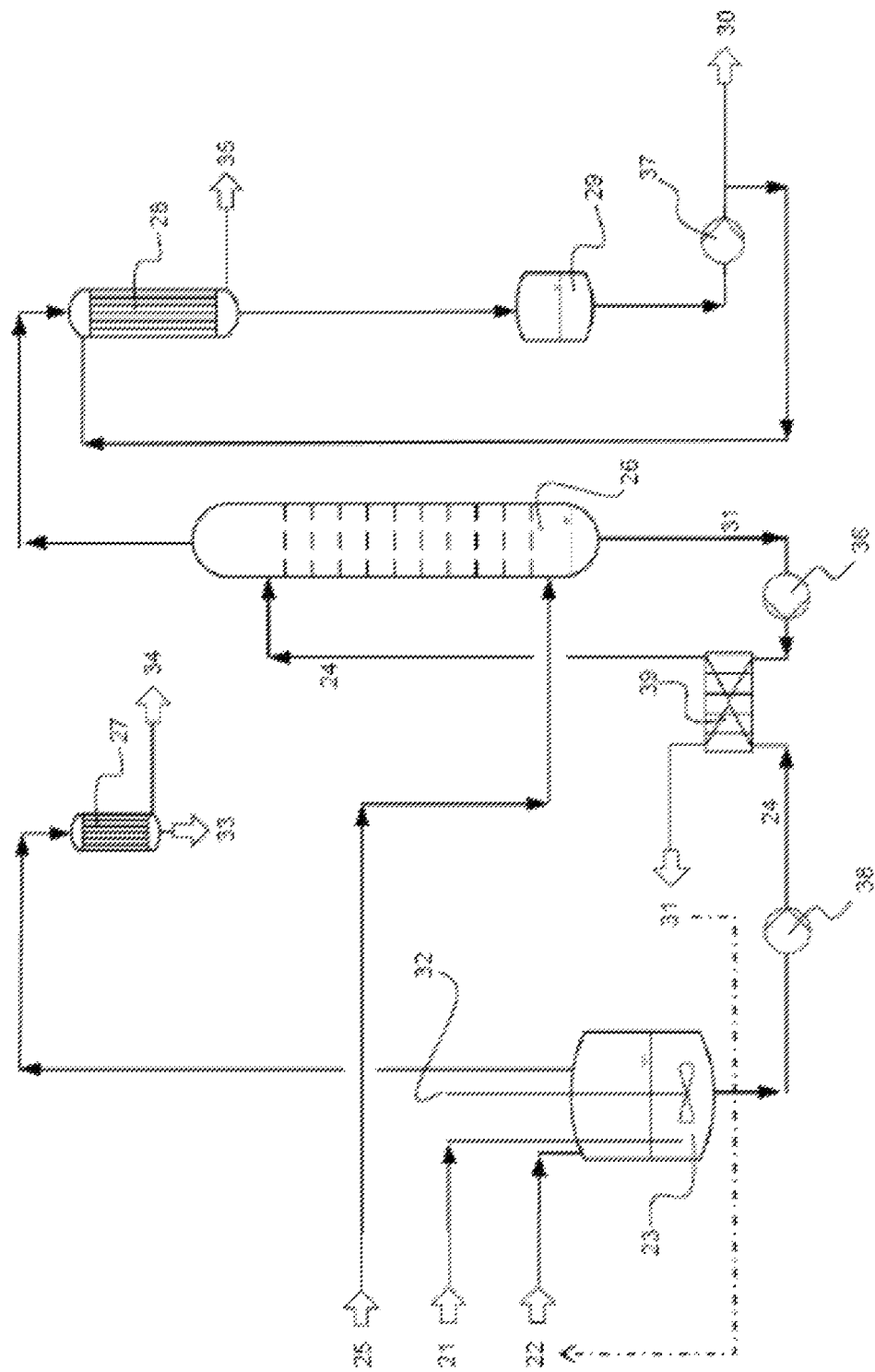

These show:

FIG. 1: schematic representation of a plant for carrying out a process according to the invention in co-current operation FIG. 2: schematic representation of a plant for carrying out a process according to the invention in countercurrent operation FIG. 1 schematically shows a plant for carrying out a process according to the invention in co-current operation. The plant comprises a first reactor 3 and a second reactor which is configured as reactive distillation device and comprises an evaporator 19 and a gas/liquid separation device 6. The first reactor 3 is equipped with a stirrer 12 and has an inlet for the introduction or addition of an aqueous sugar solution along the arrow labeled number 1. Moreover, the first reactor 3 according to FIG. 1 has a further inlet for the introduction of organic salts with a melting point <180° C. and a boiling point >200° C. at 1013.25 hPa and optionally for the introduction of additionally one or more catalysts along the arrow labeled number 2. Arranged on the first reactor 3 is a distillation device with a condenser 7. The distillation device is designed, as a result of gas removal, to evacuate the first reactor 3 in the direction of arrow 14 and to separate off water in the direction of arrow 13. The plant moreover comprises a device for removing an intermediate product mixture prepared in the first reactor 3 and/or a fraction of an intermediate product mixture prepared in the first reactor along the arrow labeled number 4 in the direction of the evaporator 19 of the second reactor. This set-up comprises a pump system 18 and devices for introducing stripping agents (compounds which can act as (carrier) gas during a subsequent distillation in the second reactor) along the arrow labeled number 5.

In the evaporator 19 of the second reactor, a mixture comprising the intermediate product mixture or a fraction of the intermediate product mixture and also the stripping agent is subjected to a further conversion and evaporation at temperatures of 165-250° C. before the resulting gas/liquid mixture is fed to the gas/liquid separation device 6 of the second reactor; the gas phase comprises the product of value HMF and the stripping agent. The product temperature in the gas/liquid separation device 6 is the same as in evaporator 19. The gas/liquid separation device 6 comprises a discharge line for dissipating a liquid distillation residue (essentially consisting of organic salt (ionic liquid) and optionally catalysts) along arrow 11. The plant is provided to introduce the distillation residue in the direction of arrow 11 via a pump system 16 of a processing unit that is not shown further, and to recycle the resulting processed organic salt in its entirety or in part along an arrow with dotted line and the arrow labeled number 2 and to return it again to the first reactor 3. The gas/liquid separation device 6, moreover, is equipped, on the top, with an outlet which is designed to condense separated-off product of value (in particular HMF) from the gas stream in a condenser 8. By means of a vacuum pump, which is not shown in FIG. 1, a subatmospheric pressure is generated in the second reactor (comprising evaporator 19 and gas/liquid separation device 6) and condenser 8 and downstream distillate container 9, where gas is drawn off in the direction of the arrow 15 and the liquid constituents (condensate) are captured in the distillate container 9. The distillate is discharged by means of a pump 17 in the direction of arrow 10. To improve the cooling performance of the condenser 8, a so-called product cooling ("quench") can optionally be used. Here, a circulatory pump is used to apply some of the cold product mixture from the distillate container 9 to the top of the condenser 8 and contributes to a more efficient condensation of the gas stream.

The mixture comprising the intermediate product mixture or a fraction of the intermediate product mixture is brought, by means of the pump system 18, prior to being introduced into the evaporator 19 of the second reactor, to a pressure increased compared to the pressure in the evaporator 19 and decompresses suddenly upon introduction into the evaporator 19 by means of a regulating valve (flash effect).

To carry out a process according to the invention for the preparation of 5-hydroxymethylfurfural (HMF), when using a plant according to FIG. 1, preferably the following steps are carried out and the following measures adopted:

An aqueous sugar solution is supplied to the first reactor 3 along arrow 1 and through the corresponding inlet; the first reactor 3 then comprises water and one, two or more starting compounds selected from the group consisting of hexoses, oligosaccharides comprising hexose units, and polysaccharides comprising hexose units. Moreover, along arrow 2 and through the corresponding inlet, one, two or more organic salts with a melting point <180° C. and a boiling point >200° C. at 1013.25 hPa, and optionally additionally one or more catalysts for the conversion of the one starting compound or at least one of the two or more starting compounds to 5-hydroxymethylfurfural (HMF) are conveyed into the first reactor 3. By means of the stirrer 12, the components conveyed to the first reactor 3 are stirred to give a starting mixture.

Even upon introducing the aqueous sugar solution to the first reactor 3, a subatmospheric pressure is present in the first reactor 3, the effect of which is that water is distilled off and transported in the direction of the condenser 7, where it condenses and is separated off in the liquid state in the direction of arrow 13. The evacuation direction is indicated by the arrow with the reference numeral 14. The starting mixture in the first reactor 3 thus comprises considerably less water than in the direction of arrow 1 and has been conveyed through the corresponding inlet in the first reactor 3. In the first reactor 3, a temperature in the range from 100 to 160° C. is adjusted, and first reaction conditions are adjusted overall in the starting mixture in the first reactor 3, and the effect of these is that a first amount of the one starting compound or at least one of the two or more starting compounds converts to HMF. An intermediate product mixture is thus formed in the first reactor 3. The intermediate product mixture is conveyed along the arrow labeled with the number 4, completely or partially, in the direction of the second reactor consisting of evaporator 19 and gas/liquid separation device 6. A stripping agent (compounds which later, i.e. in the second reactor, act as (carrier) gas)) is supplied along arrow 5 to the intermediate product mixture or its fraction. Upon entry into the evaporator 19, the resulting mixture is decompressed rapidly by means of a regulating valve (flash effect). In evaporator 19, the second reaction conditions result in a further conversion of the intermediate product mixture to HMF and in a simultaneous evaporation of the volatile components. The temperature under the second reaction conditions here is in the range from 165 to 250° C. In the gas/liquid separation device 6, the volatile product of value (in particular HMF) is separated off from the nonvolatile components with the carrier gas. The (carrier) gas here is the stripping agent in the gaseous aggregate state. For the purposes of removal by means of said carrier vapor distillation, the product mixture under the second reaction conditions is thus brought into contact, in a manner according to the invention, with a gas which comprises one or more compounds or consists of one or more compounds, where the one or more compounds have a boiling point which is lower than 200° C. at 1013.25 hPa.

The process procedure in the plant according to FIG. 1 can preferably be configured as stated above in the general part of the description.

In particular, the temperature under the second reaction conditions in the plant according to FIG. 1 (in the second reactor with evaporator 19 and gas/liquid separation device 6) can be adjusted and is in particular in the range from 180 to 250° C., preferably in the range from 190 to 250° C., preferably 200 to 240° C. The temperature under the first reaction conditions in the first reactor 3 can likewise be adjusted and is preferably in the range from 100 to 140° C. The pressure in the second reactor with evaporator 19 and gas/liquid separation device 6 can be adjusted in the plant according to FIG. 1 and is preferably under the second reaction conditions in the range from 10 to 200 mbar, preferably in the range from 10 to 100 mbar, particularly preferably in the range from 20 to 80 mbar; the pressure here is determined at the outlet of the gas stream from the condenser 8 in the vacuum pump direction (arrow 15), the pressure gradients known to the person skilled in the art prevail in the second reactor.

As already mentioned, water is removed from the first reactor and then separated off in the direction of arrow 13. A further water separation takes place in evaporator 19, during which volatile constituents are transferred to the gas phase.

The provision or preparation of the starting mixture and the conversion to the intermediate product mixture in the first reactor 3 will preferably take place in a plant according to FIG. 1 in a continuous process.

The conversion of the mixture which comprises the intermediate product mixture or a fraction of the intermediate product mixture to the product mixture will likewise preferably take place in a continuous process in a plant according to FIG. 1.

Preferably, the first reaction conditions in a plant according to FIG. 1 are adjusted such that, in the intermediate product mixture before adjusting the second reaction conditions, at most an amount of HMF is present which corresponds to a molar yield of 55 to 80%, based on the total amount of hexoses and hexose units used in the starting mixture.

Preferably, in a plant according to FIG. 1, the second reaction conditions (in the second reactor consisting of evaporator 19 and the gas/liquid separation device 6) are adjusted such that the molar total yield of HMF exceeds a value of 60%, preferably a value of 75%, particularly preferably a value of 80%, based on the total amount of hexoses and hexose units used in the starting mixture and/or the total reacted amount of hexoses or hexose units exceeds a value of 98 mol %, preferably a value of 99 mol %, based on the amount of hexoses or hexose units used in the starting mixture.

The catalyst which can be used for the conversion of the one starting compound or at least of one of the two or more starting compounds to 5-hydroxymethylfurfural (HMF) is any of the catalysts given in the general part of the description, although preference is given to using dissolved acids with a boiling point >200° C. at 1013.25 hPa, very particular preference is given to the use of methanesulfonic acid.

In a plant according to FIG. 1, each of the organic salts given in the general part of the description and having a melting point of 180° C. and a boiling point >200° C. at 1013.25 hPa (ionic liquid) can be used; the above statements relating to preferably used organic salts apply accordingly.

Shown schematically in FIG. 2 is a plant for carrying out a process according to the invention in countercurrent operation. The plant comprises a first reactor 23 and a second reactor 26. The first reactor 23 is equipped with a stirrer 32 and has an inlet for the feed line or addition of an aqueous sugar solution along the arrow labeled number 21. Moreover, the first reactor 23 according to FIG. 2 has a further inlet for the introduction of organic salts with a melting point <180° C. and a boiling point >200° C. at 1013.25 hPa, and optionally for the introduction of additionally one or more catalysts along the arrow labeled number 22. Arranged on the first reactor 23 is a distillation device with a condenser 27. The distillation device is set up to evacuate the first reactor 23 by gas removal in the direction of arrow 34 and to separate off water in the direction of arrow 33. Moreover, the plant comprises a device for removing an intermediate product mixture prepared in the first reactor 23, or a fraction of an intermediate product mixture prepared in the first reactor along the arrow labeled number 24 in the direction of the second reactor 26. This set-up comprises a pump system 38 and, however merely optionally, a heat exchanger 39. Moreover, the second reactor 26 is assigned a feed line for stripping agents (compounds which can act during a subsequent distillation in the second reactor as (carrier) gas); the introduction of the stripping agent takes place along the arrow labeled with number 25. The second reactor 26 is configured as distillation column with a number of plates for the liquid/steam equilibrium adjustment. The second reactor 26 comprises a discharge line for discharging a distillation residue along arrow 31. The plant according to FIG. 2 is intended to guide the distillation residue in the direction of arrow 31 via a pump system 36 firstly optionally via the (only optional) heat exchanger 39 (and in so doing to heat the mixture coming from the first reactor), then to introduce the distillation residue 31 along an arrow with dashed line possibly to a work-up stage and to recycle along the arrow labeled with number 22 and thus to introduce it again to the first reactor 23. The second reactor 26 is equipped on the top with an outlet which is set up to condense separated-off product of value (in particular HMF) from the gas stream in a condenser 28. By means of a vacuum pump not shown in FIG. 2, a subatmospheric pressure is generated in the second reactor 26, with gas being stripped off in the direction of arrow 35 and the liquid constituents (condensate) being captured in a distillate container 29. The distillate is discharged by means of a pump 37 in the direction of arrow 30. To improve the cooling performance of the condenser 28, optionally a so-called product cooling ("quench") can be used. Here, by means of a circulation pump, some of the cold product mixture from the distillate container 29 is applied to the top of the condenser 28 and contributes to a more efficient condensation of the gas stream.

For the purposes of carrying out a process according to the invention for the preparation of 5-hydroxymethylfurfural (HMF), when using a plant according to FIG. 2 preferably the following steps are carried out and measures adopted:

An aqueous sugar solution is supplied to the first reactor 23 along arrow 21 and through the corresponding inlet; the first reactor 23 then comprises water as well as one, two or more starting compounds selected from the group consisting of hexoses, oligosaccharides comprising hexose units, and polysaccharides comprising hexose units. Moreover, one, two or more organic salts with a melting point <180° C. and a boiling point >200° C. at 1013.25 hPa and optionally additionally one or more catalysts for the conversion of the one starting compound or at least one of the two or more starting compounds to 5-hydroxymethylfurfural (HMF) are conveyed to the first reactor 23 along arrow 22 and through the corresponding inlet. By means of stirrer 32, the components conveyed to the first reactor 23 are stirred to give a starting mixture.

Even upon introduction of the aqueous sugar solution to the first reactor 23, a subatmospheric pressure is present in the first reactor 23 and the result of this is that water is distilled off and transported in the direction of the condenser 27, where it condenses and is separated off in the liquid state in the direction of arrow 33. The evacuation direction is indicated by the arrow with the reference numeral 34. The starting mixture in the first reactor 23 thus comprises considerably less water than in the direction of arrow 21 and has been conveyed to the first reactor 23 through the corresponding inlet. In the first reactor 23, a temperature in the range from 100 to 160° C. is adjusted, and first reaction conditions are adjusted overall in the starting mixture in the first reactor 23, the result of which is that a first amount of the one starting compound or at least one of the two or more starting compounds converts to HMF. An intermediate product mixture is thus formed in the first reactor 23. The intermediate product mixture is conveyed along the arrow labeled with number 24, completely or in part, in the direction of the second reactor 26. A stripping agent (compounds which act later, i.e. in the second reactor, as (carrier) gas) is conveyed along arrow 25 at the foot or any other position of the second reactor 26 (i.e. the distillation column used as second reactor). In the optional heat exchanger 39, the intermediate product mixture can be preheated. In the second reactor 26, in the mixture that forms second reaction conditions are adjusted such that a further amount of the intermediate product mixture converts to HMF and thus forms a product mixture. The temperature under the second reaction conditions here is in the range from 165 to 250° C. and the pressure under the second reaction conditions is in the range from 10 to 200 mbar; the pressure here is determined at the outlet of the gas stream from the condenser 28 in the vacuum pump direction (arrow 35), the pressure gradients known to the person skilled in the art prevail in the second reactor. As already explained, the second reactor 26 is configured as distillation column with one or more plates. During the conversion of the intermediate product mixture or of the fractions present therein and convertible to HMF, carrier vapor distillation is used to separate off HMF from the product mixture. The (carrier) gas here is the stripping agent in the gaseous aggregate state. For the purposes of removal by means of said carrier vapor distillation, the product mixture is brought into contact under the second reaction conditions thus in a manner according to the invention with a gas which comprises one or more compounds or consists of one or more compounds, where the one or more compounds have a boiling point which is lower than 200° C. at 1013.25 hPa.

The process procedure in the plant according to FIG. 2 can preferably be designed as stated above in the general section of the description.

As regards preferred embodiments, the statements relating to FIG. 1 otherwise apply accordingly.

An essential difference between the process configuration according to FIG. 1 and the process configuration according to FIG. 2, however, is that according to FIG. 1 in the second reactor consisting of evaporator 19 and gas/liquid separation device 6, the (carrier) gas and the introduced mixture, which comprises the intermediate product mixture or a fraction of the intermediate product mixture, are conveyed co-currently, whereas in the process configuration according to FIG. 2 the (carrier) gas and the compounds which form the (carrier) gas is supplied at the bottom of the distillation column (second reactor 26), whereas the mixture which comprises the intermediate product mixture or a fraction of the intermediate product mixture is or are supplied at the top of the distillation column, so that gas and mixture move countercurrently relative to one another. Depending on the requirements of the individual case, a countercurrent operation is advantageous in some cases and a co-current operation in other cases.

EXAMPLES

Investigations Regarding the Continuous Conversion of Sugars to HMF and its Separation by Means of Carrier Vapor Distillation To carry out the examples, an apparatus according to FIG. 1 was used. The apparatus according to FIG. 1 comprised, for carrying out the examples, a continuously operated thermostated glass reactor (CSTR; first reactor 3) with two separate feeds for the starting solutions, a reflux condenser with vacuum connection for distilling off water and a discharge of the intermediate product mixture (ZPG). The evaporator 6 consisted of a thermostated glass coil with downstream thermostated gas/liquid separator, in which the volatile components are separated off as distillate by means of a cooling system consisting of metal condenser with quench device and condensed, and the nonvolatile components are excluded from the system via a bottom outlet. The second reactor was operated in vacuuo by means of a vacuum pump on the distillate side and the ZPG was decompressed in this vacuum upon entry into the second reactor 6 via a regulating valve (flash). At the same time, the stripping agent was also supplied to the evaporator via this regulating valve and in so doing decompresses into a vacuum. Consequently, the apparatus was operated in co-current procedure. All of the experiments carried out were carried out continuously and in each case it was awaited until a steady state was reached.

The temperatures given below refer to internal or product temperatures.

Starting Solutions for Preparing the Starting Mixtures:

Aqueous sugar solutions (for supplying by means of the first feed):

For examples 1, 2 and 3 and also for comparative example 4, in each case a fructose syrup was used. The content of fructose in the syrup was in each case 65% by weight in water.

For example 5, a glucose syrup was used. The glucose content was 70% by weight in water.

Solutions of other constituents (for supplying by means of the second feed):

For examples 1 to 3 and also comparative example 4, a commercial product with the name Basionic ST35 from BASF was used in pure form. Basionic ST35 is also called EMIM $CH_3SO_3$, which means 1-ethyl-3-methylimidazolium methane sulfonate. The CAS number is 145 022-45-3.

For example 5, a mixture of 98% by weight of Basionic ST35 and 2% by weight of $CrCl_3*6H_2O$ was used.

In all of the (comparative) examples 1 to 5, water vapor was used at 170° C. as gaseous stripping agent.

Further Reaction Parameters and Explanation of the Headings in Table 1:

Table 1 attached comprises details relating to the experimental parameters and the results of examples 1 to 5.

Unless stated otherwise, the examples were carried out in each case under the following parameters:
  Internal temperature of first reactor (CSTR)=130° C. (exception: comparative example 4)
  Pressure of first reactor=100 mbar (exception: comparative example 4)
  Residence time of the respective solution in the first reactor=73 min
  Mass ratio of first feed to second feed=1:3.6
  Pressure of second reactor (pump adjustment without pressure loss)=35 mbar In comparative example 4, the internal temperature in the first reactor was 61° C. and corresponded to the temperature of the individual solutions in the charge containers. The pressure in the first reactor was 1013 hPa.

The statement "Ratio gas:ZP mixture (g/g)" in table 1 refers to the ratio of the mass of the introduced (carrier) gas, i.e. steam, to the amount of ZPG which have been introduced in each case to the second reactor.

The entry in table 1 "Distillation separation efficiency ratio HMF dist/bottom (%)" is calculated as (percentage fraction of HMF in the distillate/percentage fraction of HMF in the bottom)×100.

The compositions of the respective solutions were determined by means of HPLC. The values for "conversion of sugars" arise from the residual amounts of glucose or fructose in the corresponding mixtures (ZPG, bottom and distillate), based on the molar amount of hexose used; glucose and fructose were converted to HMF and byproducts (e.g. humins). The "yield of HMF" is the ratio of the molar amount of the HMF in the ZPG, distillate or in the bottom relative to the molar amount of hexose used in each case, expressed as a percentage. The "Total yield HMF distillation" refers to the sum of the yields of HMF in distillate and bottom.

Results of the Investigations Carried Out

Examples 1-3, 5

In these experiments it was shown, irrespective of the sugar (fructose or glucose), that the total yield of HMF following distillation in the second reactor is 2-9% greater than after the first reactor (CSTR) in the intermediate product mixture.

Examples 1 and 2

Variation of the temperature in the evaporator under otherwise identical conditions. The distillation separation efficiency at 180° C. is poorer than at 200° C.

Examples 1 and 3

A reduction in the amount of vapor under otherwise identical conditions leads to a minimum impairment of the distillation performance, but is of great advantage in technical terms.

Example 1 and Comparative Example 4

Example 4 is a comparative example in which the conversion of the sugars takes place only in the evaporator under harsh conditions. Although example 4 was carried out in the apparatus described above, the CSTR was operated without external heating and without pressure and thus serves merely as a mixing section for feeds 1 and 2. The internal temperature in the CSTR corresponds, being 61° C., to the temperature of the coheated feeds 1 and 2.

The direct conversion of the sugars under harsh conditions in the evaporator (reactive distillation) without noteworthy reaction in the CSTR leads for fructose to a significantly lower yield.

Example 5

The reaction of glucose by using Cr salts as cocatalyst in the organic salt (in-situ isomerization to fructose) to HMF and the purification by means of distillation takes place with a good yield. Although the HMF yield in the ZPG after the first reactor is, as expected, lower than with fructose on account of the higher complexity of the reaction, a significant improvement in yield is likewise observed as a result of the subsequent reactive distillation.

TABLE 1

| | | First reactor (CSTR) | | Second reactor (evaporator + separator) | | | | | | |
|---|---|---|---|---|---|---|---|---|---|---|
| | | Conversion of sugar CSTR (%) | Yield of HMF CSTR (%) | Temperature of evaporator (° C.) | Ratio of gas:ZP mixture (g/g) | Conversion sugar distillation (%) | Yield HMF distillate (%) | Yield HMF bottom (%) | Total yield HMF distillation (%) | Distillation separation efficiency ratio HMF dist/bottom (%) |
| Example | Sugar | | | | | | | | | |
| 1 | Fructose | 100 | 79 | 200 | 2 | 100 | 80 | 8 | 88 | 91 |
| 2 | Fructose | 99 | 78 | 180 | 2 | 98 | 62 | 20 | 82 | 76 |

TABLE 1-continued

| | | First reactor (CSTR) | | | Second reactor (evaporator + separator) | | | | | |
|---|---|---|---|---|---|---|---|---|---|---|
| Example | Sugar | Conversion of sugar CSTR (%) | Yield of HMF CSTR (%) | Temperature of evaporator (°C.) | Ratio of gas:ZP mixture (g/g) | Conversion sugar distillation (%) | Yield HMF distillate (%) | Yield HMF bottom (%) | Total yield HMF distillation (%) | Distillation separation efficiency ratio HMF dist/bottom (%) |
| 3 | Fructose | 99 | 82 | 200 | 1 | 100 | 73 | 11 | 84 | 87 |
| 4* | Fructose | — | — | 200 | 2 | 100 | 69 | 8 | 78 | 90 |
| 5 | Glucose | 100 | 56 | 200 | 2 | 100 | 57 | 6 | 63 | 90 |

*Comparative example

The invention claimed is:

1. A process for the preparation of 5-hydroxymethylfurfural (HMF), having the following steps:
   (a) providing or preparing a starting mixture, comprising
      (i) one, two or more starting compounds selected from the group consisting of hexoses, oligosaccharides comprising hexose units, and polysaccharides comprising hexose units,
      (ii) one, two or more organic salts having a melting point <180° C. and a boiling point >200° C. at 1013.25 hPa,
      (iii) optionally one or more catalysts capable of converting the one starting compound or at least one of the two or more starting compounds to 5-hydroxymethylfurfural (HMF),
      (iv) optionally water, and
      (v) optionally further substances,
   (b) subjecting the starting mixture of (a) to first reaction conditions, such that a first amount of the one starting compound or at least one of the two or more starting compounds is converted to HMF and form an intermediate product mixture, where a temperature under the first reaction conditions is in the range from 100 to 160° C., then
   (c) subjecting the intermediate product mixture of (b) or a fraction of the intermediate product mixture of (b) to second reaction conditions, such that an amount of the intermediate product mixture converts to HMF and forms a product mixture, where a temperature under the second reaction conditions is in the range from 165 to 250° C., with HMF being separated off from the product mixture during this conversion by distillation.

2. The process according to claim 1, where
the temperature under the second reaction conditions is in the range from 180 to 250° C., and/or where
the temperature under the first reaction conditions is in the range from 100 to 140° C.

3. The process according to claim 1, where, under the second reaction conditions, HMF is separated off from the product mixture by means of carrier vapor distillation.

4. The process according to claim 1, where, for the separation by means of distillation, the product mixture is brought into contact with a gas co-currently or countercurrently under the second reaction conditions,
where the gas comprises one or more compounds having a boiling point which is lower than 200° C. at 1013.25 hPa.

5. The process according to claim 4, where the gas comprises one or more compounds selected from the group consisting of water, alcohols, monoethers, diethers, polyethers, ketones, esters, and aromatics.

6. The process according to claim 1, where the pressure under the second reaction conditions is below 1000 mbar.

7. The process according to claim 1, where
the starting mixture is prepared or provided in a first reactor and the first reaction conditions in the first reactor are established such that the intermediate product mixture is formed,
and
the intermediate product mixture is transferred, completely or in part, to a second reactor, where the second reaction conditions in the second reactor are established, and where the second reactor is a reactive distillation device.

8. The process according to claim 7, where
the intermediate product mixture or parts thereof to be transferred to the second reactor is subjected, before or upon entry into the second reactor, to the conditions of a distillation, with HMF being separated off
and/or
the reactive distillation device has an overflow valve for generating a flash vacuum effect.

9. The process according to claim 1, where
the provision or preparation of the starting mixture and the conversion to the intermediate product mixture takes place in a continuous process.

10. The process according to claim 1, where the conversion of the mixture which comprises the intermediate product mixture or a fraction of the intermediate product mixture to the product mixture takes place in a continuous, semicontinuous or discontinuous process.

11. The process according to claim 1, where a residue, present after separating off HMF, of the conversion of the intermediate product mixture to the product mixture is completely or partly recycled for use in producing the starting mixture, after separating off byproducts.

12. The process according to claim 1, where the first reaction conditions are such that
in the intermediate product mixture before establishing the second reaction conditions at most an amount of HMF is present which corresponds to a molar yield of 55 to 80%, based on the total amount of hexoses or hexose units used in the starting mixture.

13. The process according to claim 1, where the second reaction conditions are such that
the molar total yield of HMF exceeds a value of 60%, based on the total amount of hexoses or hexose units used in the starting mixture
and/or
the amount of hexoses or hexose units converted in total exceeds a value of 98 mol %, based on the amount of hexoses or hexose units used in the starting mixture.

14. The process according to claim 1, where the starting mixture comprises one or more catalyst capable of converting the starting compound or at least one of the two or more starting compounds to HMF, where the one or more catalyst is selected from the group consisting of acids having a boiling point >200° C. at 1013.25 hPa dispersed or dissolved in the starting mixture,
metal salts,
metal oxides,
ion exchange resins, and
zeolites.

15. The process according to claim 1, where said organic salt or one, two or all of said one, two or more organic salts has a melting point <180° C. and a boiling point >200° C. at 1013.25 hPa
is or are selected from the group of the salts with a boiling point >250° C. at 1013.25 hPa and/or
is or are selected from the group of the salts with a melting point <150° C. at 1013.25 hPa.

16. The process according to claim 1, having the following steps:
(a) providing or preparing a starting mixture in a first reactor, the starting mixture comprising
(i) one, two or more starting compounds selected from the group consisting of hexoses, oligosaccharides comprising hexose units, and polysaccharides comprising hexose units,
(ii) one, two or more organic salts with a melting point <180° C. and a boiling point >200° C. at 1013.25 hPa,
(iii) optionally one or more catalysts capable of converting the one starting compound or at least one of the two or more starting compounds to 5-hydroxymethylfurfural (HMF),
(iv) optionally water, and
(v) optionally further substances,
(b) subjecting the starting mixture of (a) in the first reactor to first reaction conditions such that the first amount of the one starting compound or at least one of the two or more starting compounds is converted to HMF and form an intermediate product mixture, where the temperature under the first reaction conditions is in the range from 100 to 160° C.,
(c) transferring the intermediate product mixture of (b) completely or in part to a second reactor, to provide a mixture comprising the intermediate product mixture or a fraction of the intermediate product mixture,
(d) subjecting the intermediate product mixture of (c) to second reaction conditions in the second reactor to convert a further amount of the intermediate product mixture to HMF and form a product mixture, where the temperature under the second reaction conditions is in the range from 165 to 250° C.,
where
during the conversion under the second reaction conditions, HMF is separated off from the product mixture by means of carrier vapor distillation, where, for the separation by means of carrier vapor distillation, the product is brought into contact under the second reaction conditions with a gas which comprises one or more compounds, where the one or more compounds have a boiling point which is lower than 200° C. at 1013.25 hPa.

17. A device comprising a first reactor and a second reactor for the preparation of 5-hydroxymethylfurfural (HMF), where the second reactor is a reactive distillation device,
where
in the first reactor an intermediate product mixture comprising HMF is prepared, the intermediate product mixture is transferred completely or in part to the second reactor, and in the second reactor further HMF is prepared from the intermediate product mixture or the transferred fraction of the intermediate product mixture, and the HMF distilled off.

18. The process according to claim 1 wherein the second conditions are such that the molar total yield of HMF exceeds a value of 75% based on the total amount of hexoses or hexose units used in the starting mixture.

19. The process according to claim 1 wherein the second conditions are such that the molar total yield of HMF exceeds a value of 80% based on the total amount of hexoses or hexose units used in the starting mixture.

* * * * *